United States Patent
Mishra et al.

(10) Patent No.: US 9,068,189 B2
(45) Date of Patent: Jun. 30, 2015

(54) **RECOMBINANT STRAIN OF *TRICHODERMA* USEFUL FOR ENHANCING NUTRITIONAL VALUE AND GROWTH OF PLANTS**

(71) Applicants: Aradhana Mishra, Lucknow (IN); Chandra Shekhar Nautiyal, Lucknow (IN)

(72) Inventors: Aradhana Mishra, Lucknow (IN); Chandra Shekhar Nautiyal, Lucknow (IN)

(73) Assignee: COUNCIL OF SCIENTIFIC AND INDUSTRIAL RESEARCH (IN)

( * ) Notice: Subject to any disclaimer, the term of this patent is extended or adjusted under 35 U.S.C. 154(b) by 0 days.

(21) Appl. No.: 14/003,376

(22) PCT Filed: Dec. 31, 2012

(86) PCT No.: PCT/IN2012/000863
§ 371 (c)(1),
(2) Date: Sep. 5, 2013

(87) PCT Pub. No.: WO2013/102934
PCT Pub. Date: Jul. 11, 2013

(65) Prior Publication Data
US 2014/0308748 A1    Oct. 16, 2014

(30) Foreign Application Priority Data
Jan. 3, 2012    (IN) ............... 10/DEL/2012

(51) Int. Cl.
*C12N 15/80*    (2006.01)
*C12N 15/04*    (2006.01)
*C12R 1/885*    (2006.01)

(52) U.S. Cl.
CPC ............... *C12N 15/80* (2013.01); *C12R 1/885* (2013.01); *C12N 15/04* (2013.01)

(58) Field of Classification Search
CPC .... C12N 9/2437; C12N 9/2445; C12P 19/02; C12P 19/14; C12Y 302/01004; C12Y 302/01021; C12Y 302/01091; Y02E 50/17
USPC .............. 435/183, 252.3, 320.1, 99; 536/23.2
See application file for complete search history.

(56) References Cited

U.S. PATENT DOCUMENTS 5,260,213 A    11/1993    Harman et al.

OTHER PUBLICATIONS

"5th Report on the World Nutrition Situation: Nutrition for Improved Development Outcomes", United Nations System, Standing Committee on Nutrition (SCN) [www.unsystem.org/scn/publications/AnnualMeeting/SCN31/SCN5Report.pdf], (Mar. 2004), 143 pgs.
"International Application No. PCT/IN2012/000863, International Search Report mailed Apr. 17, 2013", 4 pgs.
Elumalai, S., et al., "Inter-specific hybridization between *Trichoderma harzianum* and *Trichoderma viride* by protoplast fusion", Journal of Biotechnology, vol. 136, Supplement, (Oct. 2008), S267.
Hanson, L. E, et al., "Biocontrol efficacy and other characteristics of protoplast fusants between *Trichoderma koningii* and *T. virens*", Mycological Research, 106(3), (Mar. 2002), 321-328.
Mukherjee, Prasun K., et al., "TmkA, a Mitogen-Activated Protein Kinase of *Trichoderma virens*, Is Involved in Biocontrol Properties and Repression of Conidiation in the Dark", Eukaryotic Cell, 2, (Jun. 2003), 446-455.
Newell-McGloughlin, Martina, "Nutritionally Improved Agricultural Crops", Plant Physiology, 147, (Jul. 2008), 939-953.

*Primary Examiner* — Padma V Baskar
(74) *Attorney, Agent, or Firm* — Schwegman Lundberg & Woessner, P.A.

(57) ABSTRACT

The present invention relates to a novel recombinant fungal strain of *Trichoderma* sp. MTCC 5659 useful for enhancing the nutritional value and growth of plants. The invention further relates to a formulation useful as bioinoculant, wherein the said formulation comprises MTCC 5659 optionally along with a carrier. The claimed strain has been developed via the protoplast fusion technique of two parent *Trichoderma* strains and is useful for stimulating the content of amino acids, trace elements, chlorophyll and plant growth and yield attributing characters.

7 Claims, No Drawings

RECOMBINANT STRAIN OF *TRICHODERMA* USEFUL FOR ENHANCING NUTRITIONAL VALUE AND GROWTH OF PLANTS

PRIORITY CLAIM TO RELATED APPLICATIONS

This application is a national stage application under 35 U.S.C. §371 of PCT/IN2012/000863, filed Dec. 31, 2012, and published as WO 2013/102934 A1 on Jul. 11, 2013, which claims priority to Indian Application No. 0010/DEL/2012, filed Jan. 3, 2012, which applications and publication are incorporated by reference as if reproduced herein and made a part hereof in their entirety, and the benefit of priority of each of which is claimed herein.

FIELD OF THE INVENTION

The present invention relates to a novel recombinant strain of *Trichoderma harzianum* (*Hypocrea lixii*) (NBRI 0716) having accession number MTCC 5659, useful as a bioinoculant. In particular, the present invention relates to a protoplast fusant fungal strain of *Trichoderma harzianum* MTCC 5659 obtained from the fusion of protoplasts of the parent strains *Trichoderma harzianum* (*Hypocrea lixii*) having an accession number MTCC 5660 and *Trichoderma viride* having an accession number MTCC 5661. More particularly, it relates to a composition useful as a bioinoculant, wherein the said composition comprises a protoplast fusant fungal strain of *Trichoderma harzianum* having accession number MTCC 5659 optionally along with a carrier so as to stimulate content of amino acids, trace elements, an increase in chlorophyll content, plant growth and yield attributing characters.

BACKGROUND OF THE INVENTION AND DESCRIPTION OF PRIOR ART

At a fundamental level, food is viewed as a source of nutrition to meet daily requirements at a minimum in order to survive but with an ever greater focus on the desire to thrive. In the latter instance, there is an ever growing interest in the functionality of food. Functional foods have been defined as any modified food or food ingredient that may provide a health benefit beyond the traditional nutrients it contains. The term nutraceutical is defined as "any substance that may be considered a food or part of a food and provides health benefits, including the prevention and treatment of disease". Further to it, not only productivity of crop but amino acid content, mineral content is of crucial importance ultimately for human health who consumes it.

Protein energy malnutrition is the most lethal form of malnutrition and affects every fourth child worldwide. The Food and Agriculture Organization estimates that 850 million people worldwide suffer from under nutrition, to which insufficient protein in the diet is a significant contributing factor. Most plants have a poor balance of essential amino acids relative to the needs of animals and humans. The cereals such as maize, wheat [*Triticum aestivum*], rice, etc. tend to be low in Lysine, whereas legumes such as soybean and pea [*Pisum sativum*] are often low in the sulfur-rich amino acids Methionine and Cysteine. Micronutrient malnutrition, the so-called hidden hunger, affects more than half of the world's population, especially women and preschool children in developing countries (United Nations System Standing Committee on Nutrition (2004) United Nations System Standing Committee on Nutrition 5th Report on the World Nutrition Situation: Nutrition for Improved Development Outcomes. Higher level of micronutrients in plants is one way of increasing the possibility of their higher intake while consumption.

Agricultural innovation has always involved new, science-based products and processes that have contributed reliable methods for increasing productivity and sustainability. Biotechnology has introduced a new dimension to such innovation, offering efficient and cost-effective means to produce a diverse array of novel, value-added products and tools. Plant foods can serve as dietary sources of all essential amino acids and minerals required by humans. Amino acids and mineral concentrations are low in some plants, especially many staple food crops; thus, efforts are underway to increase the amino acids and minerals content of these foods as a means to ensure adequate attainment of dietary minerals in all individuals. While these efforts have included classical breeding approaches in the past, it is clear that future progress can be made by utilizing the tools of biotechnology to effect directed changes in plant mineral status. Different approaches have been developed to overcome the problem of low level of minerals, amino acids and increase in productivity of plants. Value-added output traits, such as improved nutrition and food functionality and plants as production factories for therapeutics and industrial products from a consumer perspective, the focus on value added traits, especially improved nutrition, is of greatest interest (Martina Newell-McGloughlin (2008) Nutritionally Improved Agricultural Crops. Plant Physiology, 147, 939-953). *Trichoderma* spp. is an asexually reproducing, free-living fungi that is common in soil and root ecosystems. It is one of the most exploited fungal biocontrol agents in the field of agriculture for the management of crop diseases caused by a wide range of fungal phytopathogens. *Trichoderma* species have been investigated as biological control agents for over 75 years, but it is only recently that isolates have become commercially available. These organisms have been favored because they are able to control a wide variety of phytopathogenic fungi that are of great importance to agriculture. *Trichoderma* spp. can control a wide variety of pathogens and appear in more products than any other microbe including Anti-Fungus; Binab T; Supresivit; T-22G and T-22HB; Trichopel, Trichoject, Trichodowels, and Trichoseal; TY. Products containing *Trichoderma* spp. control species of *Amillaria, Botrytis, Chondrostrenum, Colletotrichum, Fulvia, Fusarium, Monilia, Nectria, Phytophthora, Plasmopara, Psendoperonospora, Pythium, Rhizoctonia, Rhizopus, Sclerotinia sclerotiorum, Sclerotium rolfsii, Verticillium*, and wood rot fungi.

Though the available strains of *Trichoderma* obtained through selection or mutation, possess one or more desirable traits, none of them possess all the attributes to realize the full potential of the beneficial fungus. One method of combining characteristics from different fungi is protoplast fusion. Protoplast fusion allows the transfer of complex traits without having to know the genes involved, and for genetic recombination between organisms that cannot undergo sexual recombination. Therefore, the protoplast fusion technology has stimulated interest in the manipulation of *Trichoderma* as enzyme producers and bio-control agents against diverse plant pathogens (Hanson E. L. and C. R. Howell. (2002). Biocontrol efficacy and other characteristics of protoplast fusants between *Trichoderma koningii* and *T. virens*. Mycol. Res. 106:321-328).

While work on *Trichoderma* has been conducted in the past, there is no clear indication heretofore that any detailed study has been conducted to demonstrate the composition of *Trichoderma* showing increase in amino acid, trace elements, increase in chlorophyll content and yield simultaneously in plants, using this technique. Thus, there exists a problem in prior art where composition of biological agent needs to be developed for effecting increase in amino acid, trace elements, increase in chlorophyll content and yield simultaneously in plants. For the purpose, improved strains of *Trichoderma* are needed to be developed. Protoplast fusion of parent strains offers one option for the development of novel strains. Therefore, the present work is aimed to isolate protoplasts from parent *Trichoderma* strains followed by self-fusion of protoplasts for investigating the possible enhancement of amino acids, trace elements, an increase in chlorophyll content, and yield of plants. In the present invention, solution to the problems of prior art have been provided, by employing biotechnology as a tool to enhance the amino acids, trace elements, chlorophyll content, and yield of plants.

OBJECTIVES OF THE INVENTION

The main object of the present invention is thus to provide a novel recombinant strain of *Trichoderma harzianum* (*Hypocrea lixii*) (NBRI 0716) having accession number MTCC 5659 useful as a bioinoculant.

Another object of the present invention is to provide a composition useful as a bioinoculant, wherein the said composition comprising the recombinant fungal strain of *Trichoderma harzianum* accession number MTCC 5659 optionally along with a carrier.

Still another object of the present invention is to provide a recombinant strain of *Trichoderma harzianum* MTCC 5659 which can stimulate the content of amino acids, trace elements, chlorophyll, plant growth and yield attributing characters.

Yet another object of the present invention is to provide a novel strain of *Trichoderma* that has the ability to promote plant growth under field conditions.

A further object of the present invention is to develop a method for increasing the nutritional value and growth of plants by applying an agriculturally effective amount of the developed recombinant *Trichoderma* strain to a plant, of which the nutritional value and growth is to be increased, optionally along with a carrier.

SUMMARY OF INVENTION

The present invention relates to a novel recombinant strain of *Trichoderma harzianum* (*Hypocrea lixii*) (NBRI 0716) having been deposited under the accession number MTCC 5659 under the Budapest Treaty, at IMTECH, Chandigarh, India on 3 Oct. 2011, which is useful as bioinoculant. The said strain is a protoplast fusant, which exhibits the capability to stimulate the content of amino acids, trace elements, chlorophyll and plant growth and yield attributing characters. Further provided is a method of developing the said strain. The strain of *Trichoderma* MTCC 5659 is used by applying to plants, plant seeds, or soil surrounding plants under conditions effective to increase the nutritional value of the plants and growth of the plants or plants produced from the treated plant seeds.

DETAILED DESCRIPTION OF THE INVENTION

The practice of the present invention will employ, unless otherwise indicated, conventional techniques and methods used in the field of microbiology and molecular biology. Unless defined otherwise, all the technical and scientific terms used herein have the same meaning as commonly understood by one of ordinary skill in the art to which this invention belongs. Singleton et al., et al., DICTIONARY OF MICROBIOLOGY AND MOLECULAR BIOLOGY 2.sup.nd Ed, John Wiley and Sons, NY (1994) and Hale and Margham, THE HARPER COLLINS DICTIONARY OF BIOLOGY (1991) Addison Wesley Pub. Co. provides one of skill with dictionaries of many of the terms used in describing this invention. Any methods and materials similar or equivalent to those described herein can be used in the practice or testing of the present invention.

"Filamentous fungi" refers to all filamentous forms of the subdivision Eumycotina. These fungi are characterized by a vegetative mycelium with a cell wall composed of chitin, cellulose, and other complex polysaccharides. The filamentous fungi of the present invention are morphologically, physiologically, and genetically distinct from yeasts. Vegetative growth by filamentous fungi is by hyphal elongation and carbon catabolism is obligatorily aerobic. In the present invention, the filamentous fungal parent cell may be a cell of a species of *Trichoderma*, e.g., *Trichoderma harzianum* (currently also known as *Hypocrea Trichoderma viride*, or *Trichoderma koningii*.

For the purposes of the present invention, the parental strains of *Trichoderma harzianum* (*H. lixii*) (NBRI 0815) having accession number MTCC 5660 and *Trichoderma viride* (NBRI 1218) having accession number MTCC 5661 were isolated from diesel contaminated soil around CSIR-NBRI workshop, Lucknow.

As used herein, the term "*Trichoderma*" or "*Trichoderma* sp." refers to any fungal genus previously or currently classified as *Trichoderma*.

Accordingly, the present invention provides a novel recombinant strain of *Trichoderma harzianum* (*Hypocrea lixii*) (NBRI 0716) having been deposited under the accession number MTCC 5659 under the Budapest Treaty, at IMTECH, Chandigarh, India on 3 Oct. 2011. The said strain is useful as a bioinoculant.

In an embodiment of the present invention, the strain of *Trichoderma* with accession number MTCC 5659 has been developed from protoplast fusion of two parent strains of *Trichoderma harzianum* (*H. lixii*) (NBRI 0815) having accession number MTCC 5660 and *Trichoderma viride* (NBRI 1218) having accession number MTCC 5661, wherein the parent strains were deposited with MTCC on 3 Oct. 2011.

The characteristics of the three strains used in the invention are given here as under:

Morphological Characteristics of *Trichoderma viride* MTCC5661

- Optimal temperature for growth on Potato Dextrose Agar (PDA) Medium and Saltwater Nutrient Agar (SNA) Medium: 25 degree C.
- Colony radius on PDA: 30-35 mm after 72 h in darkness; on SNA: 22-31 mm;
- Does not grow at 35 degree C.
- Colonies grown on PDA for 1 wk at 25 degree C. with alternating light develops conidia in several alternating green and dull yellow concentric rings.
- Diffusing pigment not noted.
- Slight coconut dour rarely noted.
- Conidia often appeared to form at the surface of the pustule and globose in shape.

After one week at 20-25 degree C., conidia were deep green to dark green.

Produces phialides with fertile branches near the tip.

Morphological Characteristics of *Trichoderma harzianam/ Hypocrea lixii* MTCC5660

On PDA radius at 30 degree C. after 72 h in darkness: 28-41, 42-54, 55-67 mm.

On SNA, radius at 35 degree C. after 72 h in darkness: 18-32, 33-43 mm.

Appears to be a bit granular on PDA, with light green conidia distributed throughout.

Shape of conidia globose to subglobose, subglobose to ovoidal with smooth Ornamentation.

The conidia production was denser in center then towards the margins.

Slight coconut odour rarely noted.

An irregular yellow zone without conidia was present around the inoculum.

Some white pustules were also found growing on the green mat of conidia.

Produces phialides with fertile branches near the tip.

Morphological Characteristics of the Novel Recombinant Fusant *Trichoderma harzianum*: MTCC 5659

On PDA radius at 30 degree C. after 72 h in darkness: 28-41, 42-54, 55-67 mm.

On SNA radius at 35 degree C. after 72 h in darkness: 18-32, 33-43 mm.

Slight coconut odour rarely noted.

Shape of conidia globose.

Conidia are produced in dark green concentric rings.

Produces phialides with fertile branches near the tip.

The successful use of *Trichoderma* as agent for plant growth and enhancement of nutritional quality of plant will be greatly enhanced if improved strains are developed. Genetic recombination is a method for developing superior strains as compared to mutation or selection. Strains with desirable attributes can be used as parents to develop progeny with combination of attributes. Sexual stage is rare or lacking in most of the *Trichoderma* strains and conventional sexual crosses cannot be used for desirable manipulations. In this case protoplast fusion provides an alternative to sexual crosses to bring in together the desirable traits.

In another embodiment of the present invention, the protoplasts of *Trichoderma* parents' species viz., *T. harzianum* (*H. lixii*) (NBRI 0815) having accession number MTCC 5660 and *T. viride* (NBRI 1218) having accession number MTCC 5661 were prepared by the method of Prasun K. Mukherjee, Jagannathan Latha, Ruthi Hadar and Benjamin A. Horwitz (2003) TmkA, a Mitogen-Activated Protein Kinase of *Trichoderma virens*, Is Involved in Biocontrol Properties and Repression of Conidiation in the Dark. Eukaryotic cell, 2: 446-455. Progeny developed from the fused protoplasts of the parent strains were isolated and fungal cell/mass was regenerated to be used as an agent for plant growth and enhancement of nutritional quality of plants.

In still another embodiment, the effect of parents and fusant *Trichoderma* inoculation on amino acid profile of Chickpea seeds was studied. Inoculation of *Trichoderma* parents' species (MTCC 5660 and MTCC 5661) and its fusant (MTCC 5659) affected amino acid profile differentially.

In yet another embodiment, the effect of parents (MTCC 5660 and MTCC 5661) and fusant *Trichoderma* (MTCC 5659) inoculation on trace-element accumulation in Chickpea seeds was evaluated. *Trichoderma* parents' species (MTCC 5660 and MTCC 5661) and *Trichoderma* fusant (MTCC 5659) significantly affected mineral nutrients uptake in chickpea seeds.

In still another embodiment, the plant growth and yield attributing characters were studied. Inoculation of *Tricoderma* parents (MTCC 5660 and MTCC 5661) and *Trichoderma* fusant (MTCC 5659) increased shoot weight, root weight, number of pods, total seed weight and yield, as compared to un-inoculated control.

In a further embodiment, the increase in chlorophyll content was also observed in *Tricoderma* parents (MTCC 5660 and MTCC 5661) and in fusant inoculated seeds (MTCC 5659), as compared to un-inoculated control.

In another embodiment, the carriers that may be used to disperse the subject strain include all those commonly used for inoculating crops and would include carriers such as powdered sorghum grain, fermented press mud, grain, maize meal, maize cob, compost, rice husk, rice bran, wheat bran, cow dung and talc. The fungi in such compositions are at a level of about Log 6-10 cfu/g carrier. Carriers such as talc or fermented press mud are especially preferred in this process. The fungi are grown in broth to the necessary amount, and then mixed with the carrier at the desired inoculum size, followed by curing of the mixture by well-known methods.

In still another embodiment of the present invention, the concentration of fusant *Trichoderma* (MTCC 5659) used is in the range of Log 6-10 cfu/g of carrier and more preferably Log 4-12 cfu/g of carrier.

In yet another embodiment, the fusant *Trichoderma* (MTCC 5659) strain has the ability to stimulate plant growth.

In still another embodiment, the present invention provides a novel *Trichoderma* fusant strain (MTCC 5659) developed by protoplast fusion method having the ability to stimulate the concentration of amino acids, trace elements, chlorophyll content and growth of the plants.

EXAMPLES

The following examples are given by way of illustration to facilitate a better understanding of the invention and are not intended to limit the scope of the invention. It should be further understood that the detailed description while indicating preferred embodiments of the invention, is given by way of illustration only, since various changes and modifications within the spirit and scope of the invention will become apparent to those skilled in the art from the detailed description and thus, should not be construed to limit the scope of present invention.

Example 1

Protoplast Development of Parents *Trichoderma* MTCC 5660 and MTCC 5661

Potato dextrose agar medium (PDA, Difco) was used as growth medium for fungal cultures. For protoplasting, single 4 mm plugs from 7-d-old cultures were individually introduced into 100 ml lots of *Trichoderma* MTCC 5660 (carbendazim tolerance up to 10,000 ppm and temperature tolerance upto 30 min at 60° C.) and *Trichoderma* MTCC 5661 (no growth in carbendazim at 10 ppm and temperature tolerance upto 120 min at 70° C.) potato dextrose broth (PDB) at a concentration of approximately $1 \times 10^9$ spores/ml.

For the carbendazim tolerance single 4 mm plugs from 7-d-old cultures were individually introduced on PDA plates to check survival. For the temperature tolerance test spores from individually grown PDA plates were individually isolated and tested in water bath maintained at specified temperature and harvested at various time points and plated on PDA plates to check survival.

Cultures were grown for 24 h on orbital shaker at 120 rpm at $27\pm2°$ C. Hyphae of both *Trichoderma* species MTCC 5660 and MTCC 5660 were harvested separately by vacuum filtration and washed with sterile distilled water. Protoplasts were released from mycelia by enzymatic digestion at 25° C. with gentle shaking (50 rpm) in an enzyme mix containing 0.2 g of β-D-glucanase (Fluka), 0.4 g of Driselase (Sigma), and 2 mg of chitinase (Sigma); stirred for 5 min at room temperature in 70 ml of 0.7 M NaCl; centrifuged for 10 min at 10,000 rpm (centrifuge model), and sterile filtered (0.45-mm pore-size filter Axygen). Enzyme mix containing mycelia was filtered through four layers of sterile muslin cloth followed by cell dissociation sieve (Sigma, mesh size 100) and washed with 0.7 M NaCl followed by washing with ice-cold STC (sorbitol, 1.2 M; Tris [pH 7.5], 10 mM; $CaCl_2$, 50 mM (STC)).

Protoplasts were then counted with a haemocytometer and used immediately after STC washes and equal number of protoplasts from both isolates (suspended in STC) taken in a glass tube and mixed gently using cut-tip with 1.2 ml of chilled PEG A: Casein enzymatic hydrolysate (Sigma), 0.3 gm; Yeast extract powder, 0.3 gm (Sigm(polyethylene glycol (PEG, molecular weight 4000), 60%; Tris [pH 7.5], 10 mM; $CaCl_2$, 50 mM). The fusion mixture was incubated at 30° C. for 30 min and then diluted with STC and distributed in sterile petri plates. 20 ml regeneration medium (Regeneration Medium a); D.W. to 30 ml; Regeneration Medium B: Sucrose (SRL), 102.6 gm; Agar (Hi-Media), 4.8 gm; D.W. to 270 ml) was poured per plate and mixed by gentle swirling. Plates incubated at room temperature overnight and overlaid after 24 hrs with 10 ml of 1% agar containing carbendazim at a concentration of 100 ppm. Colonies obtained on regeneration medium after overlay was transferred on potato dextrose agar (PDA) to check stability.

Example 2

Selection of Protoplast Fusant *Trichoderma* MTCC 5659

PDA with selective carbendazim (100 ppm) was used to detect fusants, since in the previous experiments, *Trichoderma* strain MTCC 5660 would tolerate carbendazim up to 10,000 ppm and temperature tolerance upto 120 min at 70° C. On the contrary, *Trichoderma* strain MTCC 5661 would not growth in carbendazim at 10 ppm while having temperature tolerance upto 120 min at 70° C. All the putative fusants growing on carbendazim (100 ppm) were individually further subjected to temperature tolerance test at 70° C. Parental strains were transferred from PDA to selective media to confirm both selective tests, by growing on the carbendazim (100 ppm) and temperature tolerance test at 70° C., individually as well as in the combination. Likewise after screening over 4000 putative fusants, one stable *Trichoderma* strain fusant MTCC 5659 was selected. The prepared recombinant fungal strain i.e., *Trichoderma* fusant strain MTCC 5659 had the ability to tolerate carbendazim up to 10,000 ppm and exhibited temperature tolerance upto 120 min at 70° C.

Example 3

Preparation of Formulation from the *Trichoderma* Fusant Strain MTCC 5659

For large scale applications, the *Trichoderma* strain MTCC 5659 obtained in example 2 was grown on PDA at 28° C. for 10 days. The cultured biomass was scrapped from the PDA plates using sterile spatula. Fungal biomass from one 90 mm Petri plate was mixed thoroughly with 100 µl sterile distilled water and 10 g autoclaved talc. The talc was autoclaved thrice on consecutive days to reduce the level of contaminating microorganisms. For a homogeneous mixture, the contents were manually sieved through a 35-40 mesh screen with the help of a spatula. A slightly granular preparation of 10.0 gm commercial fine talc including the fungal biomass scrapped from PDA plates with 8% moisture was obtained.

Example 4

Application of the Developed Formulation to Seeds

The formulation prepared in example 3 was competent enough to be applied in agricultural, horticultural and consumer settings in such a manner that the inoculum provides the minimum required seed coating and effective *rhizosphere* colonization. The dried product was applied on chickpea seeds planted after homogenously re-suspending in water. Ten g talc formulation was suspend in 500 ml water and mixed to properly disperse the *Trichoderma* strain MTCC 5659 spores. Volume upto 1 liter was constituted with a solution of sticker (gum Arabic (1.5%)), to coat 100 kg seeds.

Example 5

After germination, the chickpea plants were allowed to grow for 5 months and then were harvested. Effect of parents and fusant *Trichoderma* inoculation on amino acid profile of Chickpea seeds has been shown. Inoculation of *Trichoderma* parents' species (MTCC 5660 and MTCC 5661) and its fusant (MTCC 5659) affected amino acid profile differentially, the effects were more pronounced in fusant inoculated seeds as compared to parents (Table1). The essential amino acids (EAAs), Met (112%), Phe (58%) and Lys (41%) significantly increased as compared to un-inoculated control. Similarly, the non-essential amino acids (NEAAs) like Asp acid, Gly (both 38%), Ala (21%) and Ser (13%) also significantly increased in fusant treated seeds as compared to uninoculated control and parents.

TABLE 1

Effect of *Trichoderma* parents' species (MTCC 5660 and MTCC 5661) and fusant *Trichoderma* (MTCC 5659) inoculation on amino acids (AAs) content in chick pea seeds after 4 months.

| Amino acid (mg kg$^{-1}$ dw) | Control | Parent 1 (MTCC 5660) | Parent 2 (MTCC 5661) | Fusant (MTCC 5659) |
|---|---|---|---|---|
| Methionine | 4.64$^a$ ± 0.22 | 7.91$^b$ ± 0.77 (70.53) | 8.15$^b$ ± 0.64 (75.57) | 9.82$^c$ ± 0.49 (111.56) |
| Phenylalanine | 0.97$^a$ ± 0.04 | 2.48$^b$ ± 0.95 (154.85) | 2.64$^b$ ± 0.15 (171.55) | 1.54$^a$ ± 0.12 (58.39) |
| Lysine | 1.12$^a$ ± 0.06 | 1.73$^a$ ± 0.79 (54.75) | 157$^a$ ± 0.11 (40.41) | 1.58$^a$ ± 0.19 (40.81) |
| Asparagine | 28.47$^a$ ± 1.00 | 30.19$^a$ ± 0.96 (6.06) | 32.48$^b$ ± 1.36 (14.09) | 39.19$^c$ ± 0.97 (37.68) |
| Glycine | 8.24$^a$ ± 1.00 | 9.43$^a$ ± 1.10 (14.51) | 8.29$^a$ ± 0.49 (0.62) | 11.34$^b$ ± 0.96 (37.64) |
| Alanine | 9.05$^a$ ± 1.00 | 10.73$^{ab}$ ± 0.86 (18.53) | 11.66$^b$ ± 1.06 (28.81) | 10.94$^{ab}$ ± 0.97 (20.85) |
| Serine | 15.54$^a$ ± 0.59 | 16.37$^{ab}$ ± 0.87 (5.32) | 16.94$^{ab}$ ± 1.03 (9.02) | 17.53$^b$ ± 1.00 (12.81) |

All the values are mean of six replicates ±S.D. ANOVA significant at $p \le 0.01$. Different letters indicate significant difference between control, parents and fusant treatments (DMRT, $p \le 0.05$). Values given in parenthesis represent percent induction or inhibition of particular amino acid with particular inoculant.

Example 6

Effect of *Trichoderma* parents' species (MTCC 5660 and MTCC 5661) and fusant *Trichoderma* (MTCC 5659) inoculation on trace-element accumulation in Chickpea seeds has been shown in table 2. *Trichoderma* parents' species (NBRI-0815, NBRI-1218 accession no (MTCC 5660 and MTCC 5661)) and *Trichoderma* fusant (NBRI 0716, accession no (MTCC 5659) significantly affected mineral nutrients uptake in chickpea seeds. The accumulation of nutrients like Cu (ca. 220%), Ni (ca. 96%), Se (ca. 23%), Zn (ca. 39%) and P (ca. 7%) were significantly enhanced in fusant (MTCC 5659) inoculated seeds (Table 2). Though, Se accumulation significantly increased in parent 1 (MTCC 5660) (99%) and parent 2 (MTCC 5661) (36%) followed by fusant (23%) (MTCC 5659) inoculated seeds. Interestingly, Ni and Zn accumulation decreased in parents 1 by 52% and 29% respectively, however increased in parent 2 treated seeds by 7% and 9% respectively. Zn induction was more pronounced in fusant (38%) treated plants. On the other hand P accumulation increased in all parents and fusant treated chickpea seeds in comparison to control seeds.

Example 7

Inoculation of *Tricoderma* parents viz., NBRI-0815 and NBRI-1218 having accession no MTCC 5660 and MTCC 5661 respectively and *Trichoderma* fusant (NBRI 0716 accession no. MTCC 5659) increased shoot weight, root weight, number of pods, total seed weight of 6 pots and yield as compared to un-inoculated control. Increase in chlorophyll content was also observed in *Tricoderma* parents (MTCC 5660 and MTCC 5661). However, the increase was more in fusant inoculated seeds (80%) (MTCC 5659). Similarly the inoculation of fusant significantly enhanced plant growth and yield as compared to parents inoculated chickpea plants. Treatment with fusant *Tricoderma* strain (MTCC 5659) significantly increased number of pods (70%), root dry weight (26%), shoot dry weight (151%), yield (22%) and seed weight (109%) as illustrated in Table 3.

TABLE 2

Effect of parents (MTCC 5660 and MTCC 5661) and fusant *Trichoderma* (MTCC 5659) inoculation on mineral content in chick pea seeds after 4 months.

| Mineral Contents (mg kg$^{-1}$ dw) | Control | Parent 1 (MTCC 5660) | Parent 2 (MTCC 5661) | Fusant (MTCC 5659) |
|---|---|---|---|---|
| Cu | 49.37$^b$ ± 1.22 | 150.15$^c$ ± 6.00 (204.11) | 13.16$^a$ ± 0.65 (−73.35) | 157.73$^c$ ± 5.25 (219.47) |
| Ni | 0.94$^b$ ± 0.05 | 0.45$^a$ ± 0.17 (−52.25) | 1.01$^b$ ± 0.05 (6.99) | 1.85$^c$ ± 0.15 (96.16) |
| Zn | 10.66$^b$ ± 1.12 | 7.60$^a$ ± 1.12 (−28.75) | 11.66$^b$ ± 0.80 (9.31) | 14.80$^c$ ± 1.05 (38.80) |
| Se | 0.02$^a$ ± 0.003 | 0.05$^b$ ± 0.009 (99.34) | 0.03$^a$ ± 0.002 (36.29) | 0.03$^a$ ± 0.003 (22.71) |
| P | 577.36$^a$ ± 21.43 | 637.78$^b$ ± 30.47 (10.46) | 649.70$^b$ ± 39.50 (12.53) | 618.76$^{ab}$ ± 13.12 (7.17) |

All the values are mean of six replicates ±S.D. ANOVA significant at $p \le 0.01$. Different letters indicate significant difference between control, parents and fusant treatments (DMRT, $p \le 0.05$). Values given in parenthesis represent percent induction or inhibition a particular trace elements with particular inoculant.

TABLE 3

Effect of parents (MTCC 5660 and MTCC 5661) and fusant *Trichoderma* (MTCC 5659) inoculation on plant biomass and yield in chick pea grain after 4 months.

|  | Control | Parent 1 MTCC 5660 | Parent 2 MTCC 5661 | Fusant MTCC 5659 |
|---|---|---|---|---|
| Chlorophyll content (mg g$^{-1}$ fw) | $0.99^a \pm 0.03$ | $1.44^b \pm 0.18$ (44.85) | $1.80^c \pm 0.27$ (81.08) | $1.78b^c \pm 0.17$ (79.22) |
| Shoot dry wt. (g) | $0.99^a \pm 0.11$ | $1.68^b \pm 0.13$ (68.92) | $1.74^b \pm 0.14$ (75.32) | $2.49^c \pm 0.15$ (150.96) |
| Root dry wt. (g) | $0.48^a \pm 0.03$ | $0.54^{ab} \pm 0.06$ (11.74) | $0.51^a \pm 0.04$ (6.07) | $0.61^b \pm 0.02$ (26.23) |
| No. of pods | $7.67^a \pm 0.58$ | $11.00^b \pm 1.00$ (43.48) | $9.67^b \pm 0.58$ (26.09) | $13^c \pm 1.00$ (69.57) |
| Total seed wt. (g) from-six pots | $120.81^a \pm 10.21$ | $124.82^a \pm 6.52$ (3.32) | $132.42^a \pm 3.13$ (9.61) | $251.89^b \pm 11.37$ (108.50) |
| Yield/100 seeds (g) | $13.61^a \pm 0.98$ | $15.61^{ab} \pm 0.69$ (14.72) | $16.06^b \pm 0.73$ (18.03) | $16.58^b \pm 1.98$ (21.85) |

All the values are mean of six replicates ±S.D. ANOVA significant at $p \leq 0.01$. Different letters indicate significant difference between control, parents and fusant treatments (DMRT, $p \leq 0.05$).

Advantages:

The main advantages of the present invention are:

The present composition is useful to promote plant growth.

The present composition has ability to stimulate the amino acid content in plants.

The present composition has the ability to stimulate the trace element content in plants.

The present composition has the ability to stimulate chlorophyll content in plant.

The present composition has the ability to increase the yield of plant.

We claim:

1. A novel recombinant strain of *Trichoderma harzianum* having accession number MTCC 5659.

2. A strain as claimed in claim 1, useful as a bioinoculant.

3. A strain as claimed in claim 1, wherein it is obtained by the fusion of protoplasts from the parental strains of *Trichoderma harzianum* (*H. lixii*) (NBRI 0815) having accession number MTCC 5660 and *Trichoderma viride* (NBRI 1218) having accession number MTCC 5661.

4. A strain as claimed in claim 1, wherein it is optionally used along with carriers selected from the group consisting of powdered sorghum grain, fermented press mud, grain, maize meal, maize cob, compost, rice husk, rice bran, wheat bran, cow dung and talc.

5. A strain as claimed in claim 1, wherein the concentration of the strain used is in the range of Log 6-12 cfu/g of carrier.

6. A strain as claimed in claim 1, having the ability to stimulate the content of amino acids, trace elements, chlorophyll and plant growth and yield attributing characters.

7. A process for the preparation of the strain as claimed in claim 1, wherein the steps comprising:

[a] preparing the protoplasts from *Trichoderma harzianum* and *Trichoderma viride* having accession numbers MTCC 5660 and MTCC 5661 respectively, in the presence of enzymes β-D-glucanase, driselase and chitinase;

[b] treating the protoplasts as obtained in step (a) with chilled PEG(polyethylene glycol);

[c] incubating the chilled protoplasts of step [b] at 30 degree C. for 30 min in petri plates in regeneration medium followed by incubation at temperature of 20 to 29 degree C. for 8 to 24 hours and overlaying with 10 ml of 1% agar containing carbendazim at a concentration of 100 ppm;

[d] isolating the colonies from the plates of step [c] to obtain the desired recombinant strain.

\* \* \* \* \*